(12) United States Patent
Kronberg (10) Patent No.: US 8,159,312 B2
(45) Date of Patent: Apr. 17, 2012

(54) METHOD AND SYSTEM FOR SIGNAL COUPLING AND DIRECT CURRENT BLOCKING

(75) Inventor: James W. Kronberg, Aiken, SC (US)

(73) Assignee: MedRelief Inc., Bethesda, MD (US)

( * ) Notice: Subject to any disclaimer, the term of this patent is extended or adjusted under 35 U.S.C. 154(b) by 1165 days.

(21) Appl. No.: 11/769,176

(22) Filed: Jun. 27, 2007

(65) Prior Publication Data

US 2009/0002067 A1 Jan. 1, 2009

(51) Int. Cl.
*H03H 7/00* (2006.01)
*H01G 9/155* (2006.01)
*H03H 1/02* (2006.01)

(52) U.S. Cl. .................. 333/24 C; 333/172; 361/313

(58) Field of Classification Search ............... 333/24 C, 333/172, 174; 361/312, 313
See application file for complete search history.

(56) References Cited

U.S. PATENT DOCUMENTS

| | | | |
|---|---|---|---|
| 5,217,009 A | 6/1993 | Kronberg | |
| 5,413,596 A | 5/1995 | Kronberg | |
| 5,833,712 A | 11/1998 | Kroll et al. | |
| 6,011,994 A | 1/2000 | Kronberg | |
| 6,188,274 B1 | 2/2001 | Vernon | |
| 6,321,119 B1 | 11/2001 | Kronberg | |
| 6,535,767 B1 * | 3/2003 | Kronberg | 607/72 |
| 6,627,252 B1 * | 9/2003 | Nanjundiah et al. | 427/79 |
| 6,631,294 B2 | 10/2003 | Andino et al. | |
| 6,801,102 B2 * | 10/2004 | Shamsaifar et al. | 333/174 |
| 6,847,095 B2 * | 1/2005 | Benaissa et al. | 257/601 |
| 6,907,295 B2 | 6/2005 | Gross et al. | |
| 6,961,622 B2 | 11/2005 | Gilbert | |
| 7,013,179 B2 | 3/2006 | Carter et al. | |
| 7,043,308 B2 | 5/2006 | Cohen | |
| 7,109,818 B2 * | 9/2006 | Rivkina et al. | 333/24 C |
| 7,117,034 B2 | 10/2006 | Kronberg | |
| 7,145,415 B2 * | 12/2006 | Sengupta et al. | 333/174 |
| 2004/0267333 A1 | 12/2004 | Kronberg | |

FOREIGN PATENT DOCUMENTS

EP 1431990 A2 6/2004

OTHER PUBLICATIONS

International Search Report, mailed Oct. 1, 2008, for PCT/US2008/068400, 3 pages.
Written Opinion, mailed Oct. 1, 2008, for PCT/US2008/068400, 4 pages.
Office Action from MIIP, mailed Aug. 12, 2011, for MX/A/2010/000038 (plus English translation), 7 pages.

* cited by examiner

*Primary Examiner* — Dean O Takaoka
(74) *Attorney, Agent, or Firm* — Seed IP Law Group PLLC (57) ABSTRACT

A method and class of circuit configurations for coupling low-frequency signals from one stage of an electronic apparatus to another stage, from the outside world to such a stage, or from such a stage to the outside world, through the use of a plurality of symmetrical double-layer capacitors combined with other electronic components are disclosed. The capacitors are used for signal transmission while blocking direct current, rather than for energy storage. Use of double-layer capacitors in place of more conventional capacitors permits the transmission of a much wider range of signals with far less distortion. The technology is particularly well-adapted to use in medical devices, including bioelectronic stimulators, where redundant devices are required for safety in case of single component failure while unacceptable levels of distortion may occur when conventional components are used.

45 Claims, 10 Drawing Sheets

METHOD AND SYSTEM FOR SIGNAL COUPLING AND DIRECT CURRENT BLOCKING

TECHNICAL FIELD OF THE INVENTION

The present invention relates to a signal coupling method and class of circuit configurations. In particular, the present invention relates to a method and system of signal coupling by replacing conventional film type or ceramic monolithic coupling capacitors in otherwise conventional coupling circuits with symmetrical carbon double-layer capacitors.

BACKGROUND

The phenomenon of capacitance has been known for centuries. The earliest electrical storage device, the Leyden jar, was a simple capacitor.

Figure 1A:
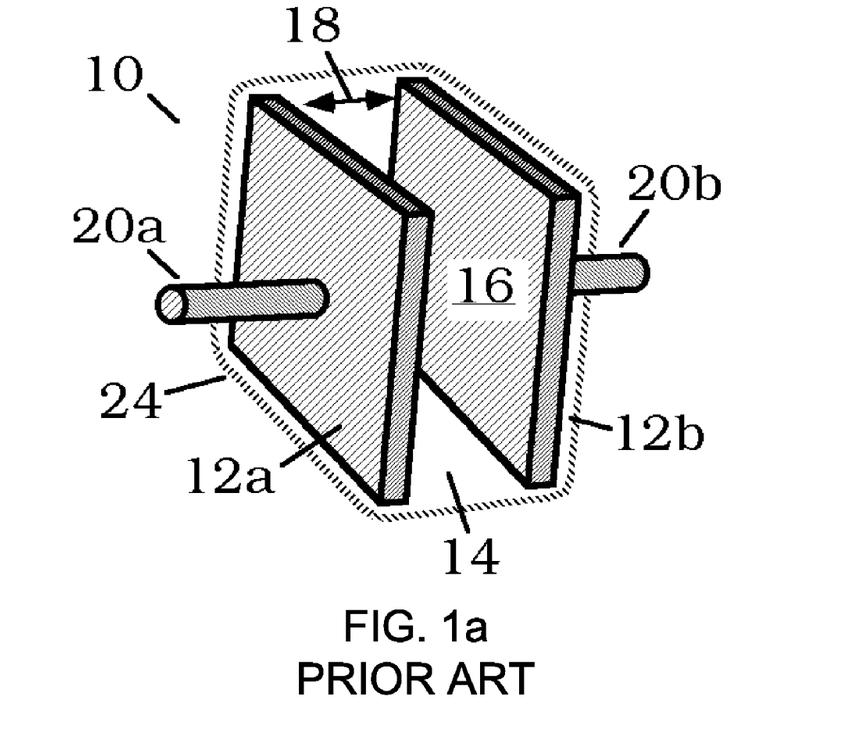
FIGS. 1a and 1b are schematic views of prior art generic capacitors.

In its simplest conceptual form, a capacitor 10 as shown in FIG. 1 may be considered as two conductive plates 12$a$ and 12$b$ set parallel with an electrically nonconductive space 14 between them. If S is the area 16 of each plate and d is the distance 18 between them, and if d is much less than the square root of S, then the capacitance value C of capacitor 10 is given by $$C = \in S/d$$

where C is in units of farads, equal to coulombs stored per volt applied, and $\in$ is the dielectric constant of whatever material fills space 14. For empty space (or approximately for most gases) the dielectric constant is $\in_0 = 8.849 \times 10^{-12}$ farad per meter. For other materials $\in$ is conveniently expressed as the product of $\in_0$ times $\in_R$, where $\in_R$ is a dimensionless number characteristic of the material. $\in_R$ typically ranges from about 2 for perfluorinated hydrocarbons such as Teflon®, through values of 3 to 6 typical of most plastics and minerals, 8.8 for aluminum oxide, 30 for tantalum oxide and 80 for distilled water, up to about 1200 for specially processed forms of barium titanate.

Figure 1B:
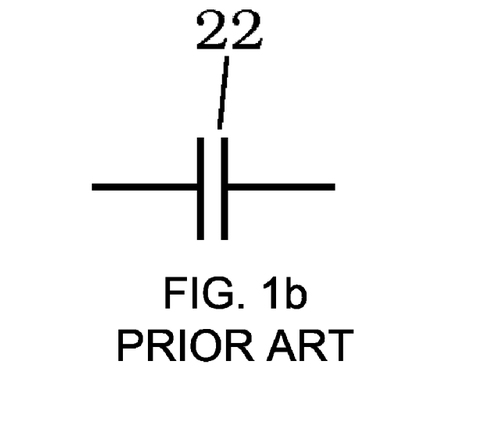

Electrical communication between a capacitor 10 and the outside world is made through two conductors 20$a$ and 20$b$, connected to plates 12$a$ and 12$b$ respectively as illustrated in FIG. 1$a$. As a result, in electronic diagrams a capacitor is represented by symbol 22 in FIG. 1$b$ representing the two plates, the space between them and the conductors leading out. Almost invariably, a practical capacitor contains in addition to these an outer insulating jacket or coating to prevent unwanted current flow or leakage, as indicated by dashed line 24 of FIG. 1$a$.

Figure 2A:
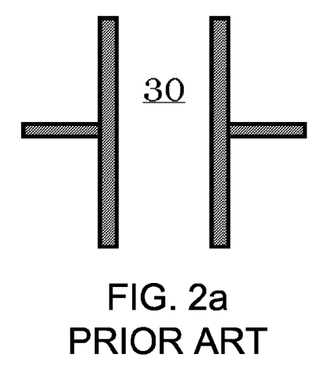
FIGS. 2a-2h are a group of schematic cross-sections of prior art capacitors made using a variety of different technologies.
Figure 2B:
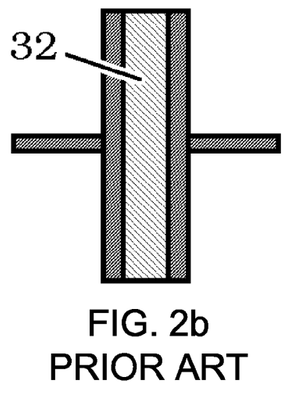

As is readily seen from the equation just given, capacitance may be increased either by increasing S, by increasing e, or by decreasing d. Early capacitors using empty space (or more practically, air) between their plates, as indicated by 30 in FIG. 2$a$, had very small values of C, on the order of a few picofarads ($10^{-12}$ farad) up to a few hundred picofarads. While useful at very high frequencies or at voltages up to many thousand volts, such capacitors find little use in other modern low-voltage electronics.

The next generation of capacitors, as illustrated in FIG. 2$b$, placed the conductive plates much closer together, separated by a thin (typically around $10^{-4}$ meter) film 32 of mica, waxed paper or plastic. Typically the plates were formed of metal foil and the film and foil were rolled together for compactness. The resulting combined increase in S, decrease in d and increase in $\in$ made practical values two to three orders of magnitude higher, from about a nanofarad ($10^{-9}$ farad) to a few hundred nanofarads, though at reduced working voltages of usually a few hundred volts.

Figure 2C:
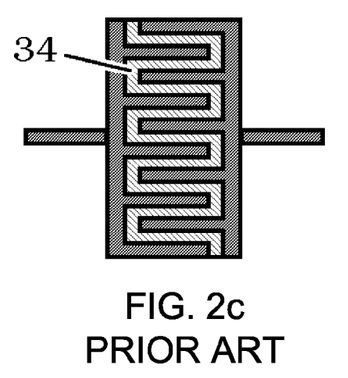
Figure 2D:
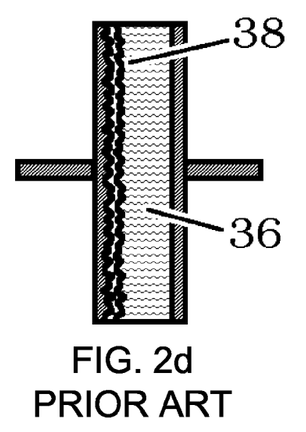
Figure 2E:
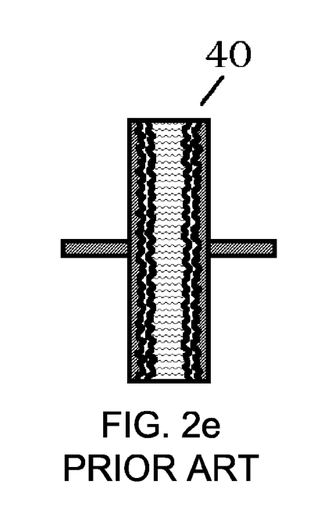

The development of ferroelectric ceramics, most of them based on specially processed barium titanate made possible a further generation of capacitors termed monolithic. Such a "chip" capacitor is built up from alternating thin (about $10^{-4}$ meter) layers of ceramic 34 and a metal such as palladium, fired together into a single ceramic piece, as illustrated in FIG. 2$c$. While practical devices are small, they are easier to manufacture than film capacitors and much more durable. The very high value of $\in_R$ in ceramic 34, typically around 1200, offsets the necessarily reduced S yielding practical values from a few nanofarads to about one microfarad ($10^{-6}$ farad) with working voltages typically of ten to thirty volts. Ferroelectric ceramics may also be used in "disk" capacitors where the ceramic replaces material 32 in the previous example, yielding smaller values of capacitance but able to operate at higher voltages.

A further development, permitting large capacitance in small volume through large S and very small d, was the electrolytic capacitor as illustrated in FIG. 2$d$. Here at least one plate is formed of a metal such as aluminum or tantalum, etched or otherwise processed to maximize its surface area, then placed in contact with an electrolyte 36. By application of a controlled current and voltage, a thin ($10^{-6}$ meter or so) layer of oxide 38 is grown on the surface and forms the dielectric. Since $\in_R$ is moderately high (though not as high as in a ferroelectric ceramic) and d is orders of magnitude thinner than would be possible in a mechanically built-up structure, capacitance values from one microfarad ($10^{-6}$ farad) to many thousand microfarads are easily achieved at working voltages ranging from a few volts to a few hundred volts.

The development of electrolytic capacitors revolutionized electronics by making relatively large capacitance values economically achievable. Electrolytics have a downside, however, in that they are inherently unidirectional or polarized. This results from the manufacturing process and the chemistry of the metal and electrolyte. So long as the applied voltage has the same polarity of that used to form the oxide layer originally, the capacitor functions as intended. If the voltage is reversed, however, the oxide layer breaks down and the capacitor becomes extremely leaky resulting essentially in a short circuit. This requires special precautions in the use of electrolytic capacitors, limiting their usefulness to applications such as power storage in which the applied voltage is always of the same, correct polarity.

It is worth pointing out that processing both plates of an electrolytic capacitor 40, rather than just one, as illustrated in FIG. 2$e$, can yield a device with approximately symmetrical characteristics. Such symmetrical electrolytic capacitors are occasionally used in signal processing, for example in low-impedance audio applications such as filters and graphic equalizers. Because of the greater complexity of manufacture and resulting high relative cost, however, symmetrical electrolytic capacitors 40 are often a last resort when nothing else will serve. A more common approach is simply to place two conventional, polarized electrolytic capacitors of equal value back-to-back in series. Leakage through each capacitor in its reverse direction quickly charges their common point to a high enough voltage to prevent further reverse biasing, and the pair then functions approximately as would a single, symmetrical capacitor having one-half the rated value of each component.

Figure 2F:
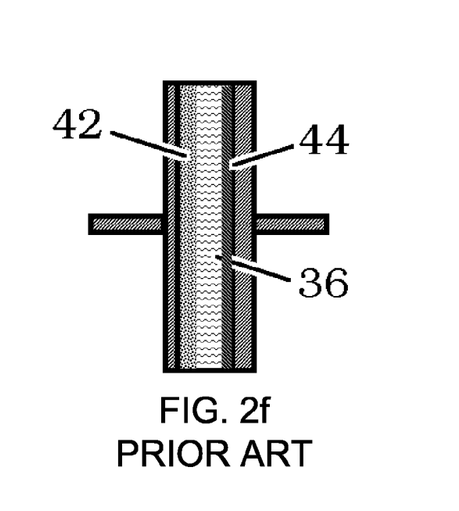

The newest development in capacitors, and forming part of the invention described below, is the so-called "ultracapacitor," "supercapacitor," "double-layer" or "electrochemical" ("EC") capacitor. This is broadly similar to an electrolytic capacitor illustrated in FIG. 2e, but instead of a layer of metal oxide, it depends for its "dielectric" on the surface barrier potential which arises at any junction between a semiconductor such as carbon and another material. As illustrated in FIG. 2f when the second material is an electrolyte 36, this barrier arises through the spontaneous formation of a so-called "double layer" in which one layer is formed by mobile electrons in the carbon 42 and the other by mobile ions in the electrolyte 36. Voltage applied across this double layer draws the opposite charges apart, leaving a thin empty zone which forms the dielectric.

Because this layer is very thin, often less than a nanometer ($10^{-9}$ meter), and because the surface area S of a body of activated carbon or carbon aerogel is extremely high, practical capacitance values in devices of this sort range from a minimum of about 0.05 farad (50,000 microfarads) upward to many farads. The downside arises from this same thinness: a single capacitor of this type is limited, depending on its construction and the liquid forming the dielectric, to a maximum working voltage of no more than two or three volts. For higher voltages, multiple units must be connected in series.

In early double-layer capacitors only one body of porous carbon 42 was used, one wire connected to it through a metal plate backing the carbon, and the other wire to a metal can lined with specially processed nickel 44 in direct contact with the electrolyte. Such a device, as illustrated in FIG. 2f, has properties like those of an electrolytic capacitor (illustrated in FIG. 2e): operating in only one polarity, and liable to damage or destruction if voltage is applied the wrong way. Its nickel content 44 also makes it relatively costly and requires special handling in disposal due to possible toxic release.

Figure 2G:
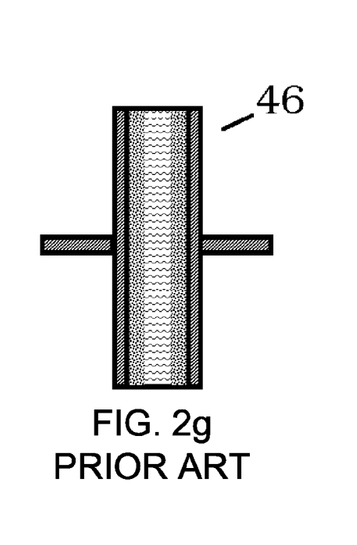
Figure 2H:
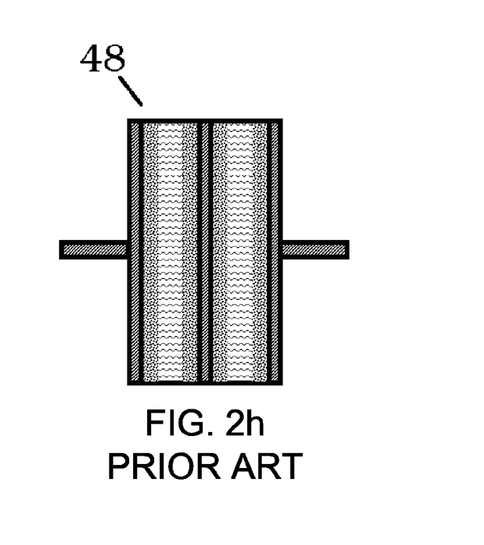

Since about the turn of the twenty-first century, however, advances in technology have made it simpler and more economical to attach carbon to both plates of a symmetrical double-layer capacitor 46 rather than just one. Such a capacitor is illustrated in FIG. 2g. The resulting capacitors are suitable for mass production and prices are rapidly dropping. Working voltage per cell is typically two to three volts, with higher voltages attainable by connecting two or more cells in a series stack 48 as illustrated in FIG. 2h. Small units suitable for printed circuit board mounting are now commercially available at prices as low as about $1.00 each in quantity. One such series of devices is the ELNA "Dynacap" DX series, comprising 0.047, 0.1, 0.22, 0.33 and 1.0-farad devices all rated at 5.5 volts.

It is not generally recognized, however, that the new, symmetrical characteristics of these carbon-carbon double-layer capacitors 48 permit uses far beyond those of energy storage. A likely cause is the fact that the previous generations of high-valued capacitors, such as electrolytic capacitors, were almost exclusively unidirectional and easily damaged by reversed polarity. Since the electrical double layer is made possible with the carbon-electrolyte junction, it is not subject to such damage. If it is in any way disrupted, it can re-form virtually instantly. In a modern symmetrical double-layer capacitor 48, having two plates coated with porous carbon, one plate becomes active and provides high capacitance in one polarity while the other acts essentially as a short circuit, while in the opposite polarity their roles are reversed.

Figure 3A:
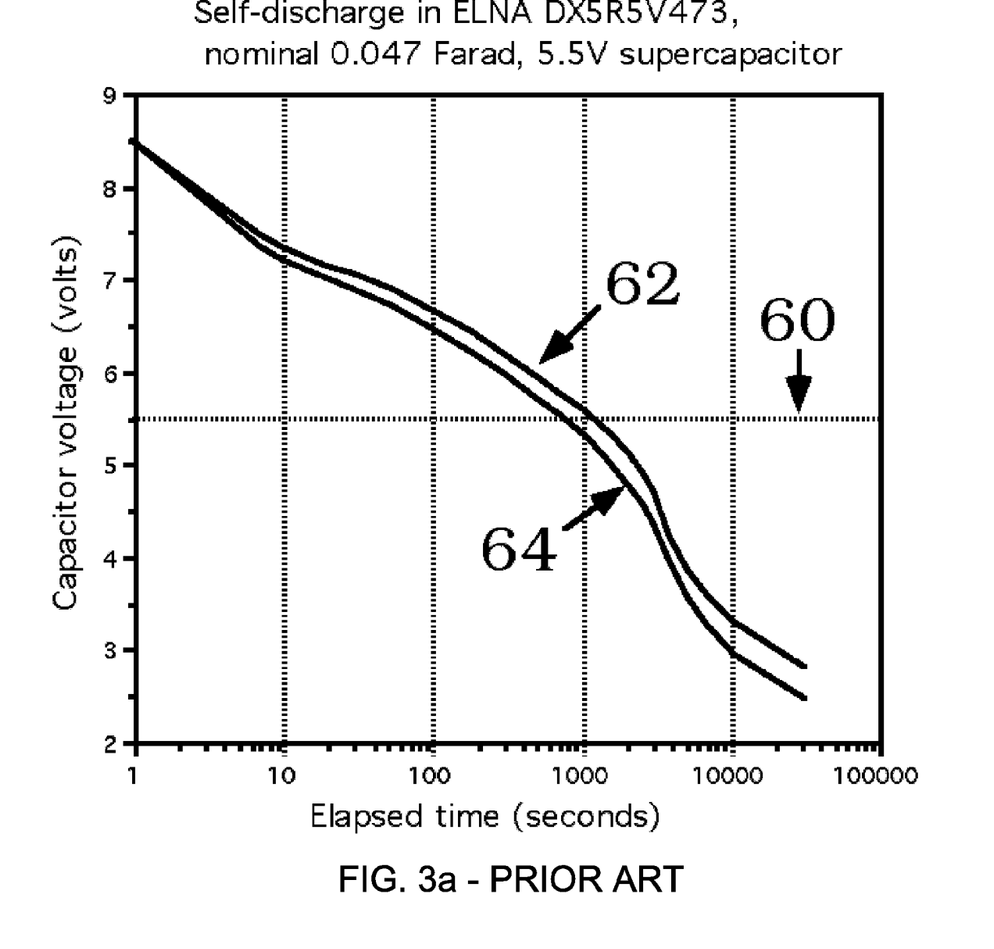
FIGS. 3a-3b are a pair of graphs showing the self-discharge characteristics and calculated internal leakage currents in a conventional, commercially available double-layer capacitor.

For example, FIG. 3 illustrates the self-discharge curves measured for a typical ELNA DX-5R5V473 "Dynacap" (0.047 farad, 5.5 volts) capacitor 48 in both the marked "forward" and marked "reverse" directions. In each case, the capacitor 48 was charged from a 9-volt alkaline radio battery through a 100-ohm resistor until a connected voltmeter read 8.50 volts, well above the rated Dynacap maximum working voltage of 5.5 volts, indicated by line 60 in FIG. 3a. The battery was then disconnected. The capacitor voltage was measured at increasing intervals and plotted against the logarithm of time. Smooth curves 62 and 64 were then fitted to the nominal "forward" and "reverse" data points respectively as illustrated in FIG. 3a.

Figure 3B:
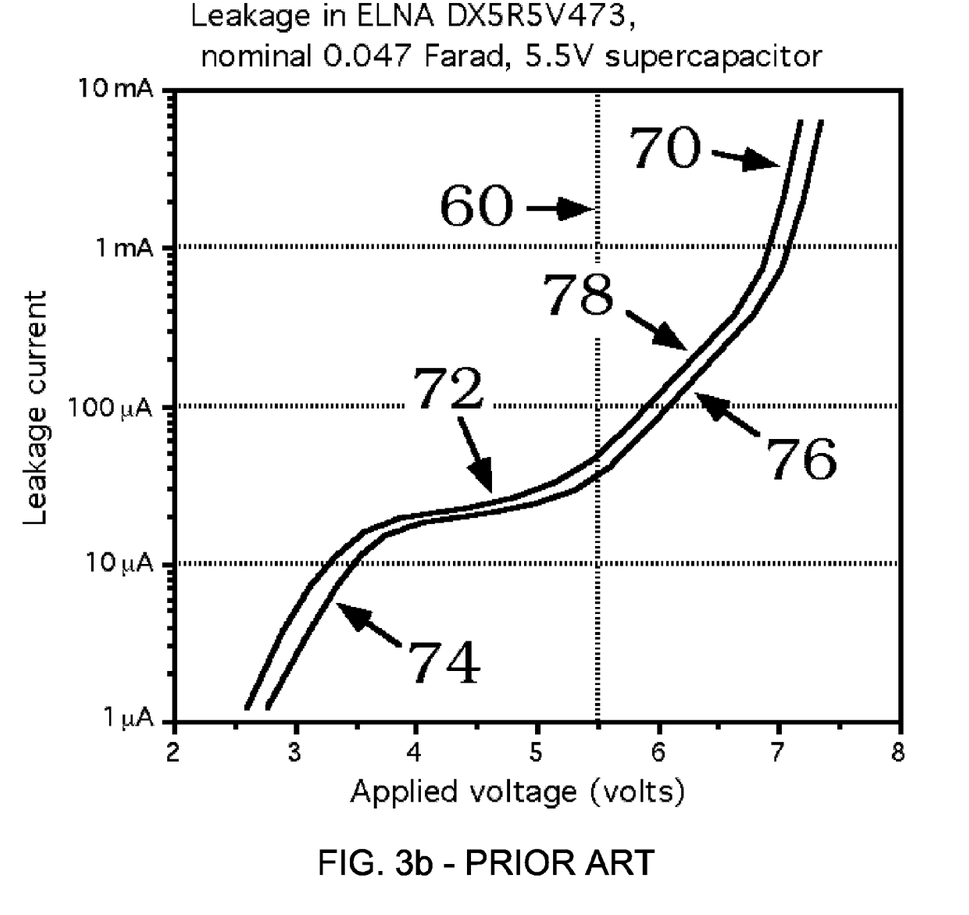

From the change in voltage between successive data points the internal leakage current was then found from the relationship $$I_{lkg}=C\Delta V/\Delta t=0.047\ \Delta V/\Delta t$$

and plotted logarithmically as a function of voltage. As seen in FIG. 3b, the leakage drops from relatively high values near point 70 (above the rated voltage line 60) to about forty microamperes at the rated voltage, then reaches a plateau (near point 72) at about twenty microamperes over the range of four to five volts. Below four volts, the leakage drops again to lower values (around point 74). There is a difference between marked "forward" leakage values 76 and marked "reverse" values 78, but this difference is never more than a factor of two across the rated working voltage range.

One typical application for capacitors is capacitive coupling. Specifically, capacitive coupling is the transfer of electrical energy from one circuit element to another circuit element using the capacitance between the circuit elements. Capacitive coupling is typically achieved by placing a capacitor in series with the signal to be coupled. Such a capacitor may be called a coupling capacitor. A coupling capacitor is used to connect two circuits such that only the alternating current (AC) signal from the first circuit can pass through to the next while direct current (DC) is blocked. This technique may be used to avoid altering the DC bias settings of each circuit when they are interconnected. Thus capacitive coupling is also known as AC coupling.

A coupling capacitor may be known as a DC blocking capacitor. Capacitive coupling has the disadvantage of degrading the low frequency performance of a system containing capacitively coupled units, since each coupling capacitor along with the input impedance of the next stage forms a high-pass filter and each successive filter results in a cumulative filter. Thus, for adequate low frequency response, the coupling capacitor usually must have high enough capacitance so that the reactance (at the lowest frequency of interest) is much higher than the input impedance of the next stage. Poor low-frequency performance of a coupling capacitor can complicate the transfer of A/C electrical signal having long time constants.

Prior art devices, for example the bioelectronic stimulators described In U.S. Pat. Nos. 5,217,009, 5,413,596, 6,011,994, 6,321,119, 6,535,767 7,117,034, and U.S. Published Application No. 20040267333, all of which are here incorporated by reference, have required the use of back-to-back electrolytic capacitors for output direct current blocking. With capacitors of practical size, however, successful coupling is limited to signals having small unbalanced charge content at any given time. Those with significant unbalance even for a relatively short period may become distorted.

As such, there is a need in the art for capacitive coupling circuits with very good low frequency performance. Such low frequency performance can sustain efficient signal propagation where the signals may have long time constant components. There is also a need for such capacitive coupling to substantially block the transfer of direct current signal components while maintaining acceptable low frequency performance. Also, there is a need in some cases, especially in medical applications, for such a capacitive coupling circuit to contain series redundant elements for safety considerations.

SUMMARY OF THE INVENTION

A method and class of circuit configurations are described for coupling low-frequency signals from one stage of an electronic apparatus to another stage, from the outside world to such a stage, or from such a stage to the outside world, through the use of one or more double-layer capacitors. The double-layer capacitors can be combined with other, readily available and low-cost electronic components used in electronic circuit design, such as resistors.

One important feature of the invention is the use of compact, economical symmetrical double-layer capacitors for signal transmission, as distinguished from energy storage. The method may be beneficial for introducing signals from electronic apparatus into biological materials, such as the living human or animal body, other organisms, or cells or tissues in culture. The use of double-layer capacitors, providing higher values of capacitance in devices of practically small size and cost, can permit the transmission of a potentially much wider range of signals with far less distortion while still blocking any significant direct current.

Another important feature is that the double-layer capacitors can be connected in the path of signal flow with both capacitor terminals floating, rather than as usual with double-layer capacitors having at least one terminal connected to ground or another point of fixed voltage. This permits the passage of alternating-current components of a signal through the capacitors from one stage of an electronic apparatus to another stage, from the outside world to such a stage, or from such a stage to the outside world, while blocking any direct current component. This feature can be important especially in bioelectronic stimulators and similar medical devices, in which any net direct current applied to living tissue can cause harmful electrolytic reactions.

Another important feature of the invention is the use of multiple, discrete double-layer capacitor devices connected in series, regardless of whether each such device comprises a single cell or a stack of two or more, while maintaining adequate capacitance for successful coupling. For example, two such devices could be connected in series.

The new symmetry of double-layer capacitors opens them to new field of applications in which double-layer capacitors, especially in values of one farad or lower, can be used in the same way as other nonpolarized capacitors yet with exceptionally extended timing characteristics due to their orders-of-magnitude higher values. For example, such capacitors can be used to couple exceptionally low-frequency alternating current (A/C) signals, such as on the order of 20 Hz or less at ordinary impedance levels, or low audio frequencies in the 100 Hz range when unusually low impedances are used or when distortion must be minimized for some medical applications. Other low frequencies can include, but are not limited to, a 5-15 Hz band, as well as 0.00056 Hz (reversing every 15 minutes, full cycle every 30, —which signal generation technique is often referred to as the Borgens application for nerve regrowth), and frequencies as low as 0.0001 Hz. Additional low frequencies can include, but are not limited to, one Hertz (Hz), one-tenth, three tenths, one hundredth, three hundredths, one thousandth, three thousandths, one ten-thousandth, and three ten thousandths of a Hertz. However, other low frequencies are not beyond the scope of the invention.

The capacitors can couple these low frequency A/C signals from one stage of an electronic apparatus to another stage, from the outside world to such a stage, or from such a stage to the outside world, while still blocking any direct-current components of such signals and without the need to ensure a specific, unchanging polarity exists across the capacitor.

In particular, this field of applications includes the coupling of low-frequency signals between electronic apparatus and the human or animal body, cells, tissues or complete organisms in culture for purposes of diagnosis, treatment, the acceleration of growth or healing, or other purposes in the art of electrobiology and electrostimulation without the accompanying risk of electrolytic effects from prolonged exposure to signals which may inadvertently contain some direct current component.

In any medical device sold in the U.S., the United States Food and Drug Administration requires that safety be maintained regardless of any possible single-component failure. A simple way to satisfy this requirement is the "rule of three" where any critical component is made triply redundant with any two of the three subcomponents sufficient for safe operation. Triply redundant output capacitors placed in series can be used to support safe operation of any medical device while still maintaining low signal distortion.

Alternatively, where signals are sufficiently high in voltage to require it, more than three discrete devices might be used so that all operate within their specified voltage ranges.

Yet another important feature of the invention is the use of double-layer capacitors along with relatively low-valued resistors to match the impedances of typical biological materials while maintaining long time constants, such as on the order of seven, sixteen, thirty-six, one hundred twenty, one hundred fifty, five hundred, twelve hundred, and fifteen hundred seconds, just to name a few examples. Other values for long time constants can include, but are not limited to, ones on the order of ten, thirty, one hundred, three hundred, one thousand, three thousand, or potentially as long as ten thousand seconds.

For an applied voltage or current step capacitively coupled into a resistive load, the decay time, or time for the signal to decline to 1/e or about 36.8% of its original value, is given by $$T=(R_1+R_2+R_3+\ldots)(1/C_1+1/C_2+1/C_3+\ldots)$$

where $R_1$, $R_2$, $R_3$, etc. and $C_1$, $C_2$, $C_3$, etc. are resistances and capacitances all connected in series. If all the individual resistance values are replaced by a single equivalent series resistance $R_S$, and all the individual capacitances by a single equivalent series capacitance $C_S$, the decay time is simply given by $$T=R_S C_S$$

and thus to maintain a given desired decay time, if $R_S$ decreases $C_S$ must increase by a proportional amount. Where $R_S$ is small, as in most biological materials or systems, a large $C_S$ is required for satisfactory transmission. The use of double-layer capacitors, especially in a redundant "rule of three" configuration, permits this maintenance of long time constants noted above provided the value of each capacitor is sufficiently high to offset the loss caused by connecting multiple capacitors in series.

For example, the resulting coupling circuits permit the economical achievement of exceptionally long time constants (on the order of on the order of ten, thirty, one hundred, three hundred, one thousand, three thousand or potentially as long as ten thousand seconds) and large charge displacements (on the order of 0.25 coulomb) and thus the coupling of exceptionally low frequencies or signals containing such low-frequency components, especially those below 20 Hz, for example into biological materials for purposes of diagnosis, treatment or the acceleration of growth or healing while still blocking any direct current component of the signals.

The discussion of capacitive coupling circuits presented in this summary is for illustrative purposes only. Various aspects of the present invention may be more clearly understood and appreciated from a review of the following detailed description of the disclosed embodiments and by reference to the drawings and the claims that follow. Moreover, other aspects, systems, methods, features, advantages, and objects of the present invention will become apparent to one with skill in the art upon examination of the following drawings and detailed description. It is intended that all such aspects, systems, methods, features, advantages, and objects are to be included within this description, are to be within the scope of the present invention, and are to be protected by the accompanying claims.

Many aspects of the invention can be better understood with reference to the above drawings. The elements and features shown in the drawings are not to scale, emphasis instead being placed upon clearly illustrating the principles of exemplary embodiments of the present invention. Moreover, certain dimensions may be exaggerated to help visually convey such principles. In the drawings, reference numerals designate like or corresponding, but not necessarily identical, elements throughout the several views.

DETAILED DESCRIPTION OF EXEMPLARY EMBODIMENTS

The invention can be embodied in many different forms and should not be construed as limited to the embodiments set forth herein; rather, these embodiments are provided so that this disclosure will be thorough and complete, and will fully convey the scope of the invention to those having ordinary skill in the art. Furthermore, all "examples" or "exemplary embodiments" given herein are intended to be non-limiting, and among others supported by representations of the present invention.

The invention includes a method and class of circuit configurations for coupling low-frequency signals from one stage of an electronic apparatus to another stage, from the outside world to such a stage, or from such a stage to the outside world, through the use of one or more preferably a plurality of double-layer capacitors, combined with other, readily available and low-cost electronic components such as resistors. The double-layer capacitors can be connected in the path of signal flow with both capacitor terminals floating, contrary to the conventional usage of double-layer capacitors where at least one terminal is connected to ground or some other fixed voltage potential. The invention can be applied to the field of bioelectronic stimulation, in which a signal of specific strength and waveform is applied to a biological material to elicit a desired response such as the acceleration of growth or healing.

An example of an output section for a conventional bioelectronic signal generating device is described in U.S. Pat. No. 6,535,767, the entire contents of which are hereby incorporated by reference, and is illustrated in FIG. 4.

There are three redundant resistors in series that include 100, 102, and one that is selected from a group of resistors 104a, 104b and 104c as determined by the position of switch 106. Values of these resistors are calculated so that, if any one of them should fail as a short circuit, the remaining two, together with other distributed resistances in drivers 108 and elsewhere in the circuit, will suffice to limit currents at output terminals 110 to safe levels. Resistors alone, however, cannot by themselves distinguish an alternating current from a direct current signal and thus cannot ensure that the signal at terminals 110 is charge-balanced (i.e., has no D.C. component) as is also required for safe use.

Diodes 103 and 105 are not essential to circuit operation, but provide a visual or electronic indication that current is flowing. At least one of these diodes, shown in the figure as 105, is a light-emitting diode (LED) which may be either a visible LED, or the infrared LED in an optical isolator providing electronic input, for example, to a microprocessor. Alternatively, both diodes 103 and 105 may be LEDs. With the diodes arranged in an antiparallel (non-parallel) manner as shown (in which the anode of each is tied to the cathode of the other), the pair is able to pass a high-frequency signal and emit light in proportion to the current flowing. This provides an indication simultaneously that the battery is providing adequate operating voltage, that all circuit blocks which it powers are functioning correctly, and that current is properly flowing to the load connected at terminal 110.

Figure 4:
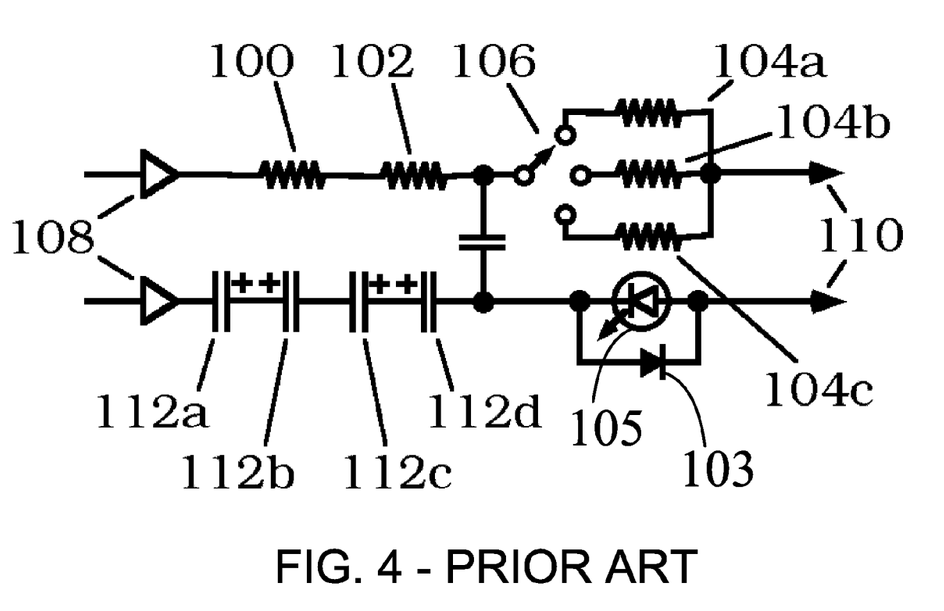
FIG. 4 is the schematic diagram of the output section of a prior art bioelectronic stimulator using redundant electrolytic capacitors.

Also in FIG. 4, are capacitors 112a, 112b, 112c and 112d. These respectively form two back-to-back pairs, so that if any one of them fails the other unit which is connected in the same polarity can still suffice to block direct current from the output and thus ensure safe operation.

Unfortunately, when capacitors are connected in series in this way the total capacitance is given by $$C_S = 1/((1/C_1 + 1/C_2 + 1/C_3 + \ldots))$$

where $C_1$, $C_2$, $C_3$, etc. are the individual capacitances so connected. When all units are of equal value, this expression becomes simply $$C_S = C/N$$

where N is the number of individual units and C is the value of each. For 10-microfarad units connected in a string of four in this manner, the resulting series value is thus only 2.5 microfarads. With the string placed in series with a typical biological load of 500 ohms the resulting decay time constant is only 1.25 milliseconds, severely limiting the range of signals and frequencies which may be applied. Longer time constants, and thus a broader frequency range of operation, can be achieved using larger-valued capacitors, but at the penalty of increased size, bulk, cost and weight.

Figure 5:
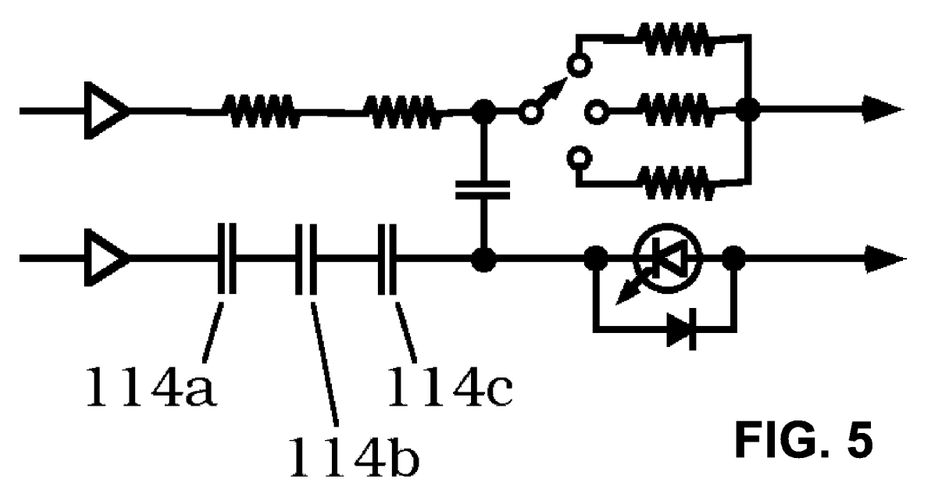
FIG. 5 is the schematic diagram of the same output section reconfigured using double-layer capacitors following the "rule of three" according to one exemplary embodiment of the invention.

In FIG. 5, the same output coupling section of FIG. 4 is shown redrawn using double-layer capacitors according to the present invention. At least three such capacitors 114a, 114b and 114c are used, thus satisfying the "rule of three." Unit working voltages are chosen so that in the event of failure of any capacitor as a short circuit, the remaining units together will still safely block any direct current signal component without exceeding their rated voltages. For example, with a 9-volt maximum applied signal, three 5.5-volt double-layer capacitors such as those in the ELNA DX series of capacitors may be used, any two sufficing for safe operation.

Using the lowest-valued device in the DX Series, the DX5R5V473 whose characteristics were shown in FIG. 3, each device has a capacitance of 0.047 farad and thus the string of three has a series capacitance of about 0.0157 farad: 15,700 microfarads, or more than 6000 times that of the equivalent string in FIG. 4. Again applying a signal through such a string to a typical biological load of 500 ohms, the resulting time constant is 7.83 seconds. Still longer time constants are readily achievable using other devices from the same series or from others like it having standard, 10% tolerance stock values as indicated in Table 1. For example, longer time constants can include, but are not limited to, ones on the order of seven, sixteen, thirty-six, one hundred twenty, one hundred fifty, five hundred, twelve hundred, and fifteen hundred seconds (as shown in Table 1), just to name a few examples. Other values for long time constants can include, but are not limited to, ones on the order of ten, thirty, one hundred, three hundred, one thousand, three thousand, or potentially as long as ten thousand seconds. Therefore, some time constants supported by the invention can range from between ten to ten-thousand seconds and, other ranges, such as between one hundred and one-thousand seconds.

This opens up a broad new range of low-frequency A/C signaling, such as on the order between 20 Hz. and 0.0001 Hz., which may prove to be of great value in bioelectronic stimulation. Additional low frequencies can include, but are not limited to, one Hertz (Hz), one-tenth, three tenths, one hundredth, three hundredths, one thousandth, three thousandths, one ten-thousandth, and three ten thousandths of a Hertz. However, other low frequencies are not beyond the scope of the invention.

TABLE 1

Capacitor Values and related Time Constants

| Single capacitor value (farads) | Value of three capacitors in series (farads) | Time constant with 500 ohms in series (seconds) |
|---|---|---|
| 0.047 | 0.0157 | 7.83 |
| 0.10 | 0.0333 | 16.7 |
| 0.22 | 0.0733 | 36.7 |
| 0.33 | 0.110 | 50 |
| 1.0 | 0.333 | 150 (2.5 minutes) |
| 3.3 | 1.10 | 500 (8.33 minutes) |
| 10 | 3.33 | 1500 (25 minutes) |

For example, it has been shown by Richard Borgens, Director of Purdue Center for Paralysis Research, and others that nerve regrowth is stimulated by a very low-frequency square wave in which the polarity is reversed approximately every fifteen minutes. Using three double-layer capacitors each with a value of ten farads, connected in series, would permit the introduction of such a signal into a 500-ohm typical biological load without unacceptable signal distortion yet without exposing the treated tissues to possible damaging electrolytic effects.

Low frequencies produced by the invention can include, but are not limited to, a 5-15 Hz band, as well as 0.00056 Hz (reversing every 15 minutes, full cycle every 30, —which signal generation technique is often referred to as the Borgens application for nerve regrowth), and frequencies as low as 0.0001 Hz. Additional low frequencies can include, but are not limited to, one Hertz (Hz), one-tenth, three tenths, one hundredth, three hundredths, one thousandth, three thousandths, one ten-thousandth, and three ten thousandths of a Hertz. However, other low frequencies are not beyond the scope of the invention. However, other low frequencies are not beyond the scope of the invention.

Figure 6A:
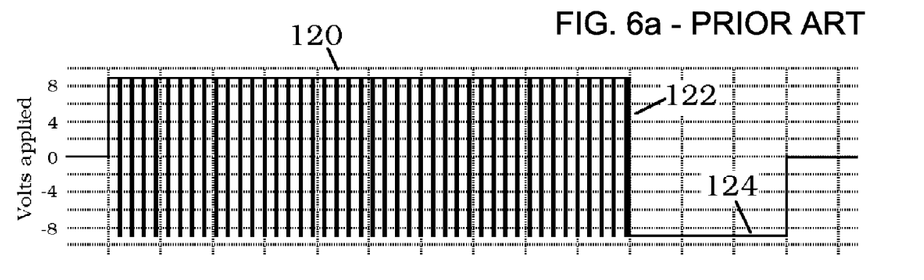
FIGS. 6a-c are comparisons of waveforms coupled into a standard test load, simulating the impedance of a typical biological system, using the coupling methods of FIGS. 4 and 5 according to one exemplary embodiment of the invention.

FIG. 6 illustrates and compares the signal coupling characteristics of the prior art output section in FIG. 4 with that in FIG. 5 embodying the invention. Trace 120 of FIG. 6a shows the differential output voltage from drivers 108. The signal takes the form of a train 122 of short, asymmetric pulses, followed by an equalizing pulse 124 which, since made approximately equal to the difference between times spent at positive and negative polarities within train 122, restores electrical balance for zero net charge (no D.C. content). Since with practical components it cannot be assured that no failure or value change will affect this balance, however, capacitive D.C. blocking is still required for safety. Desirably, the same voltage pattern in trace 120 would be reproduced almost unchanged across the biological material being treated.

Figure 6B:
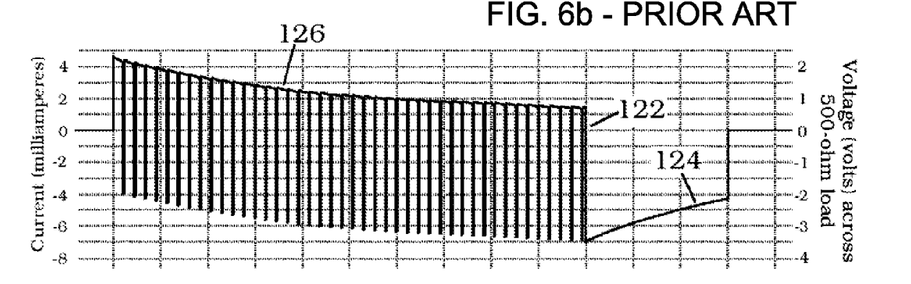

Trace 126 of FIG. 6b of the prior art shows the signal from the output section appearing across a 500 ohm resistance, representing a typical biological load, placed between terminals 110. The distortion introduced by the combination of capacitors 112a through 112d is clearly seen in the form of voltage droop along the length of train 122, resulting in positive pulses diminishing in strength over time while the negative pulses increase in strength. All pulses are noticeably distorted in shape as well, with equalizing pulse 124 dramatically so.

Figure 6C:
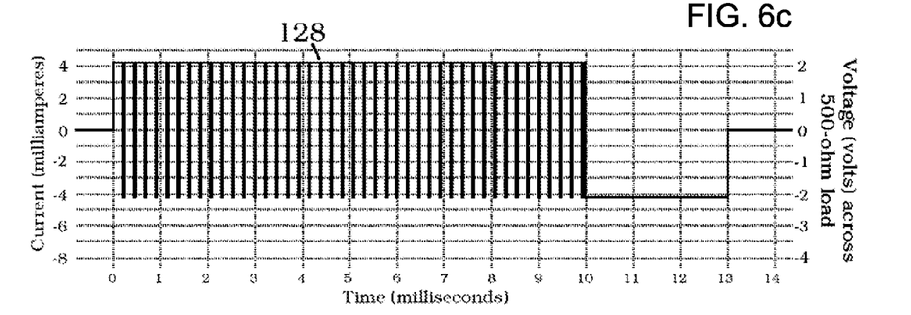

Trace 128 of FIG. 6c of one embodiment of the invention, shows the same signal when capacitors 122a through 122d have been replaced with three double-layer capacitors 124a through 124c as detailed above. As can be seen, there is no detectable distortion between the applied voltage and that appearing across the load.

Figure 7:
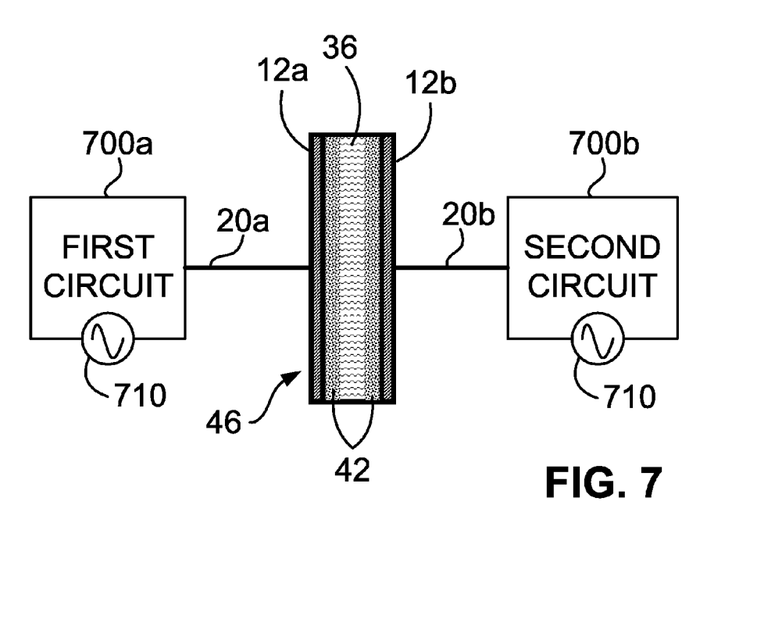
FIG. 7 illustrates a double layer capacitor coupling a signal between a first circuit and a second circuit according to one exemplary embodiment of the invention.

Referring now to FIGS. 7 and 8, FIG. 7 illustrates a double layer capacitor 46 coupling a signal 710 between a first circuit 700a and a second circuit 700b according to one exemplary embodiment of the invention. The conductors 20a and 20b operate to interconnect the first circuit 700a to the coupling capacitors 46 and the coupling capacitors to the second circuit 700b. This interconnection provides a conductive pathway for alternating current (A/C) electrical signals 710 from one circuit to the other through the double layer capacitors 46.

The capacitor 46 may substantially block the direct current (D.C.) components of any signals 710 that it couples between the first circuit 700a and the second circuit 700b. However, the capacitor 46 can couple a substantial portion of the other low frequency energy contained within A/C signals 710 that the capacitor 46 operates to couple between the first circuit 700a and the second circuit 700b.

The double layer capacitors can comprise any capacitor exhibiting symmetrical double layer characteristics, for example a two sided carbon super capacitor 46 as illustrated. Alternatively, although usually less desirable, each capacitor shown may be replaced with two identical, asymmetrical supercapacitors in a back-to-back configuration analogous to that of a capacitor pair as illustrated in FIG. 4. As discussed with relation to FIG. 2g, such a capacitor can achieve the desired double layer when one layer is formed by mobile electrons in the carbon 42 and the other by mobile ions in the electrolyte 36. A voltage of the correct polarity applied across this double layer draws the opposite charges apart, leaving a thin empty zone which forms the dielectric of the capacitor. More generally, the dielectric is based on the surface barrier potential which arises at any junction between a semiconductor such as carbon and another material.

Figure 8:
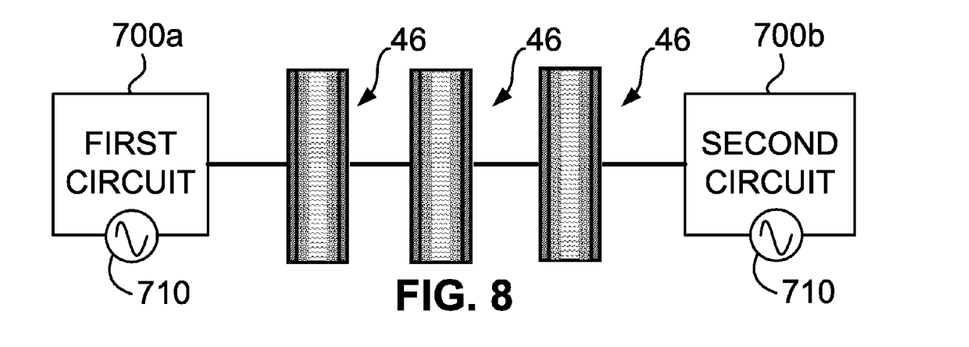
FIG. 8 illustrates three double layer capacitors in series coupling a signal between a first circuit and a second circuit according to one exemplary embodiment of the invention.

The double layer capacitor can also comprise a stacked capacitor 48 as discussed with respect to FIG. 2h. Multiple capacitors placed in series may also be used as shown in FIG. 8. The capacitors illustrated in FIG. 8 may each be dual layer capacitor units 46 as shown or each may be stacked double layer capacitors cells 48 having two, three, or more than three cells per stacked capacitor 48 (See FIG. 2h). Series, and/or stacked, capacitors can provide for redundancy in the signal path, protecting the load from the failure of one or more of the individual capacitors 46. An example of such redundancy is the "rule of three" as discussed above.

In an exemplary embodiment (not illustrated), the circuit 700a can be coupled to dual layer capacitor units 46 which are coupled to biological material. The biological material can comprise a living organism. For example, the living organism can comprise tissue, cells in culture, a living human body, a living animal other than human, and other like living organisms.

While the capacitors illustrated in FIGS. 7 and 8 are illustrated as parallel plate 12a and 12b capacitors, they may have any other geometry or electrochemical make-up known in the art to achieve a double-layer, super capacitor, or ultracapacitor effect. Examples of other geometries may be wrapped coils, concentric plates, stacked plates, radially interleaved plates, plates with surfaces treated or textured to increase surface area. Materials within the capacitors 46 may include any combination of carbon, silicon, geranium, gallium arsenide, doped semiconductors, combinations thereof, or any other semiconductor; electrolytic liquids, gases, electrolytic gels, electrolytic pastes, electrolytic solids, electrolytic matrix, or any such electrolytic materials; and metal or oxide layers such as copper, nickel, aluminum, alloys, any other conductors, metal oxides, silicon oxides, or any alloys or combinations thereof, as examples.

Figure 9:
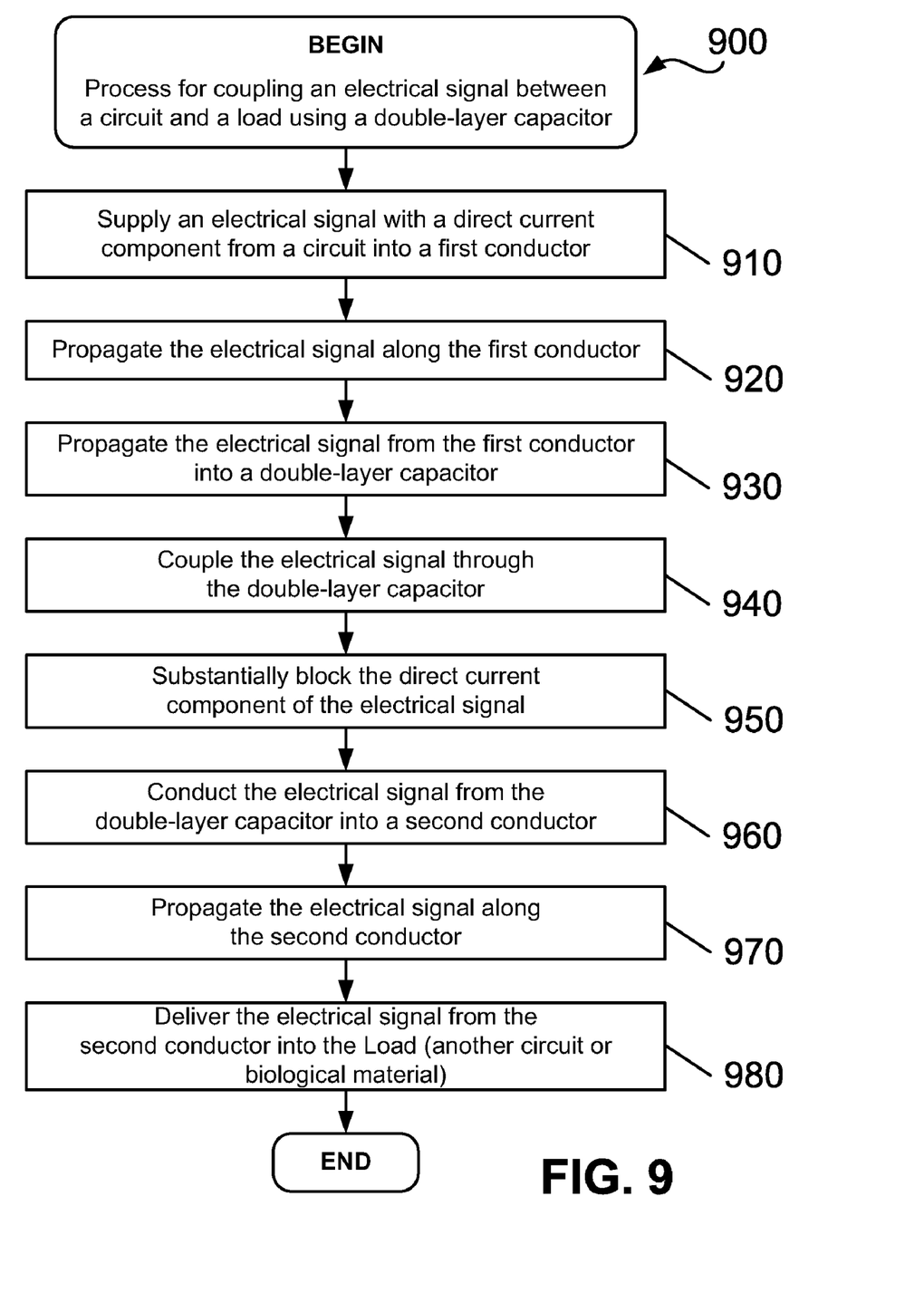
FIG. 9 is a logical flow diagram of a process for coupling an A/C electrical signal between two circuits using a double layer capacitor according to one exemplary embodiment of the invention.

Turning now to FIG. 9, this figure illustrates a logical flow diagram 900 of a process for coupling an A/C electrical signal between a circuit and a component using a double layer capacitor according to one exemplary embodiment of the present invention. The component can comprise another circuit or biological material. Certain steps in the processes or process flow described in all of the logic flow diagrams referred to below must naturally precede others for the invention to function as described. However, the invention is not limited to the order of the steps described if such order or sequence does not alter the functionality of the invention. That is, it is recognized that some steps may be performed before, after, or in parallel with other steps without departing from the scope or spirit of the invention.

The method 900 using double-layer capacitors to couple an A/C electrical signal between a circuit and a component can begin with Step 910 where an A/C electrical signal 710 from a first circuit 700a is supplied into a first conductor 20a.

Next, in Step 920, the A/C electrical signal 710 is propagated along the first conductor 20a. This conductor may be in electrical communication between the first circuit 700a and the double-layer coupling capacitor 46.

Next, in Step 930, the A/C electrical signal 710 is conducted from the first conductor 700a into a double-layer capacitor 46. This capacitor 46 is used here as a coupling capacitor. The double-layer capacitor 46 may be a solitary capacitor cell demonstrating double capacitor characteristics, or it may be a series connection of one or more of such capacitors, or it may be one or more stacked capacitors 48. Such double layer capacitors may be also be known as super capacitors or ultracapacitors.

Next, in Step 940, the A/C electrical signal 710 is coupled through the double layer capacitor 46. Coupling the A/C electrical signal through the double layer capacitor 46 may be considered as the propagation of the alternating current components of the A/C electrical signal 710.

In Step 950, any direct current (D.C.) components of the A/C electrical signal 710 are substantially blocked from being coupled through the capacitor 46. In Step 960, the A/C electrical signal is conducted from the double-layer capacitor 46 into a second conductor 20b. The second conductor 20b can be in electrical communication with the second plate 12b of the capacitor 46.

Next, in Step 970, the A/C electrical signal 710 is propagated along the second conductor 20b. Finally, in Step 980 the A/C electrical signal 710 is delivered from the second conductor 20b into a component such as second circuit 700b of FIG. 8 or a component such a biological material. The delivered signal should be substantially similar to the signal originally supplied in Step 910, however, any direct current (D.C.) components will have been substantially blocked by the double-layer capacitor 46. The delivery of the A/C signal may demonstrate excellent low-frequency performance and thereby be beneficial for conducting signals 710 with long time-constant components.

For example, longer time constants supported by the invention can include, but are not limited to, ones on the order of seven, sixteen, thirty-six, one hundred twenty, one hundred fifty, five hundred, twelve hundred, and fifteen hundred seconds, just to name a few examples. Therefore, some time constants supported by the invention can range from between five to seventy-two hundred seconds and, other ranges, such as between one hundred fifty and twelve hundred seconds. Low-frequency A/C signals supported by the invention can include, but are not limited to, signals with frequencies such as on the order between 20 Hz. and 0.0001 Hz.

This step of coupling the A/C electrical signal through the double layer capacitor 46 may couple low frequency components of the A/C electrical signal 710 more effectively than a single-layer capacitor 30 couples the low frequency components of the A/C electrical signal 710.

The foregoing description is considered as illustrative only of the principles of the invention. Since numerous modifications and changes will readily occur to those skilled in the art, it is not desired to limit the invention to the exact construction and operation shown and described, and accordingly, all suitable modifications and equivalents may be resorted to, falling within the scope of the invention. Thus, it will be apparent to those skilled in the art that many changes and substitutions can be made to the preferred embodiment herein described without departing from the spirit and scope of the present invention as defined by the appended claims. Furthermore, the scope of the present invention is to be limited only by the claims that follow.

What is claimed is:

1. A coupling circuit comprising:
   a first conductor in electrical communication with a first external circuit;
   a second conductor in electrical communication with a second external circuit;
   a double-layer capacitive element between the first conductor and the second conductor and coupling an electrical signal between the first external circuit and the second external circuit, the double-layer capacitive element further operable to substantially block a direct current (DC) component of the electrical signal; and
   a resistor in communication with the double-layer capacitive element, the resistor operable to improve impedance matching between the first external circuit and the second external circuit.

2. The coupling circuit of claim 1, wherein the double-layer capacitive element includes a semiconductor in contact with an electrolytic material.

3. The coupling circuit of claim 1, wherein the double-layer capacitive element includes a first semiconductor in contact with an electrolytic material, and a second semiconductor in contact with the electrolytic material.

4. The coupling circuit of claim 1, wherein the double-layer capacitive element includes a plurality of double-layer capacitors connected in series.

5. The coupling circuit of claim 1, wherein the double-layer capacitive element includes one or more ultracapacitors.

6. The coupling circuit of claim 1, wherein the electrical signal includes an unbalanced charge.

7. The coupling circuit of claim 1, wherein the resistor and the double-layer capacitive element produce a time constant.

8. The coupling circuit of claim 1, wherein the resistor and the double-layer capacitive element produce a time constant in excess of ten seconds.

9. The coupling circuit of claim 1, wherein the resistor and the double-layer capacitive element produce a time constant in excess of thirty seconds.

10. The coupling circuit of claim 1, wherein the resistor and the double-layer capacitive element produce a time constant in excess of one-hundred seconds.

11. The coupling circuit of claim 1, wherein the resistor and the double-layer capacitive element produce a time constant in excess of one-thousand seconds.

12. The coupling circuit of claim 1, wherein the resistor and the double-layer capacitive element produce a frequency at approximately or below twenty Hertz.

13. The coupling circuit of claim 1, wherein the resistor and the double-layer capacitive element produce a frequency approximately between five and fifteen Hertz.

14. The coupling circuit of claim 1, wherein the resistor and the double-layer capacitive element produce a frequency approximately between one and three ten thousandths of a Hertz.

15. A method comprising the steps of:
   supplying a signal including both an alternating current (AC) component and a direct current (DC) component into a first conductor;
   propagating the signal along said first conductor into a double-layer capacitive element and a resistor that is coupled to the double-layer capacitive element, the resistor being operable to improve impedance matching between a circuit and a load;
   coupling the AC component of the signal through said double-layer capacitive element;
   blocking the DC component of the signal with said double-layer capacitive element;
   propagating the AC component of the signal from said double-layer capacitive element into a second conductor; and
   delivering the AC component of the signal from the second conductor to the load.

16. The method of claim 15, wherein propagating the signal along said first conductor into a double-layer capacitive element includes coupling the signal through a single double-layer capacitor.

17. The method of claim 15, wherein propagating the signal along said first conductor into a double-layer capacitive element includes coupling the signal through a plurality of double-layer capacitors.

18. The method of claim 15, wherein delivering the AC component of the signal from the second conductor to the load includes delivering the AC component of the signal from the second conductor into a biological material.

19. The method of claim 15, wherein delivering the AC component of the signal from the second conductor to the load includes delivering the AC component of the signal from the second conductor into another circuit.

20. A coupling circuit for propagating an alternating current (AC) signal between two elements, the coupling circuit comprising: a double-layer capacitive element connected in a path of signal flow between the two elements, wherein a direction of the path of signal flow is from an electronic apparatus to biological material from a living organism, and the double-layer capacitive element includes terminals, each terminal operating in a floating state relative to one of ground and a fixed voltage; and a resistor in communication with the double-layer capacitive element, the resistor operable to improve impedance matching between the first external circuit and the second external circuit.

21. The coupling circuit of claim 20, in which the two elements are part of the electronic apparatus, and said path of signal flow is from one stage of the electronic apparatus to another stage.

22. The coupling circuit of claim 20, in which another direction of said path of signal flow is from an external environment to the electronic apparatus.

23. The coupling circuit of claim 20, in which another direction of said path of signal flow is from the electronic apparatus to an external environment.

24. The coupling circuit of claim 20, in which said biological material is from a living human body.

25. The coupling circuit of claim 20, in which said biological material is from a living animal body.

26. The coupling circuit of claim 20, in which said biological material is from a living organism other than a human or an animal.

27. The coupling circuit of claim 20, in which said biological material is from biological cells in culture.

28. The coupling circuit of claim 20, in which said biological material is from tissues in culture.

29. The coupling circuit of claim 20, wherein the double-layer capacitive element comprises a plurality of cells connected in series.

30. The coupling circuit of claim 20, further comprising a plurality of double-layer capacitive elements that each include a plurality of cells connected in series.

31. The coupling circuit of claim 20, in which said one or more double-layer capacitive elements are used along with resistors to produce a frequency at approximately or below twenty Hertz.

32. The coupling circuit of claim 20, in which said one or more double-layer capacitive elements are used along with resistors to produce a frequency below twenty Hertz.

33. The coupling circuit of claim 20, in which said one or more double-layer capacitive elements are used along with resistors to produce a frequency approximately between five and fifteen Hertz.

34. The coupling circuit of claim 20, in which said one or more double-layer capacitive elements are used along with resistors to produce a frequency approximately between one and three ten thousandths of a Hertz.

35. A coupling circuit for propagating an alternating current (AC) signal between two elements, the coupling circuit comprising:
a double-layer capacitive element connected in a path of signal flow between the two elements, wherein a direction of the path of signal flow is from an electronic apparatus to biological material from a living organism, and the double-layer capacitive element includes terminals, each terminal operating in a floating state relative to one of ground and a fixed voltage wherein the AC signal is accompanied by a direct current (DC) signal component and includes unbalanced charge content.

36. The coupling circuit of claim 35, in which said unbalanced charge content exists for a period of time.

37. A coupling circuit for propagating an alternating current (AC) signal between two elements, the coupling circuit comprising: one or more double-layer capacitive elements connected in a path of signal flow between the two elements, wherein said one or more double-layer capacitive elements are used along with resistors to match an impedance of a biological material while maintaining a time constant that has a magnitude greater than six seconds, the one or more double-layer capacitive elements including terminals that operate in a floating state relative to one of ground and a fixed voltage.

38. The coupling circuit of claim 37, in which said time constant has a magnitude greater than thirty seconds.

39. The coupling circuit of claim 37, in which said time constant has a magnitude greater than 100 seconds.

40. The coupling circuit of claim 37, in which said time constant has a magnitude greater than 300 seconds.

41. The coupling circuit of claim 37, in which said time constant has a magnitude greater than 1000 seconds.

42. The coupling circuit of claim 37, in which said time constant has a magnitude greater than 3000 seconds.

43. The coupling circuit of claim 37, in which said time constant has a magnitude greater than 10,000 seconds.

44. A coupling circuit for propagating an alternating current (AC) signal between two elements, the coupling circuit comprising:
a plurality of double-layer capacitive elements connected in a path of signal flow between the two elements, wherein a direction of the path of signal flow is from an electronic apparatus to biological material from a living organism, and each of the double-layer capacitive elements include respective terminals a plurality of cells connected in series, each terminal operating in a floating state relative to one of ground and a fixed voltage; in which said plurality of double-layer capacitive elements includes three double-layer capacitors.

45. The coupling circuit of claim 44, wherein said plurality of double-layer capacitive elements includes double-layer capacitors operating within their specified voltage ranges.

* * * * *